United States Patent
Heagle et al.

(10) Patent No.: US 8,216,198 B2
(45) Date of Patent: Jul. 10, 2012

(54) CANISTER FOR RECEIVING WOUND EXUDATE IN A NEGATIVE PRESSURE THERAPY SYSTEM

(75) Inventors: David Heagle, Taunton, MA (US); E. David Fink, Franklin, MA (US); Scott Wudyka, Marlborough, MA (US); Arnaz S. Malhi, Watertown, MA (US); David R. Swisher, St. Charles, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 299 days.

(21) Appl. No.: 12/472,465

(22) Filed: May 27, 2009

(65) Prior Publication Data
US 2010/0179493 A1    Jul. 15, 2010

Related U.S. Application Data

(60) Provisional application No. 61/143,449, filed on Jan. 9, 2009.

(51) Int. Cl.
*A61M 1/00*    (2006.01)

(52) U.S. Cl. .................. 604/319; 604/313; 604/540

(58) Field of Classification Search .............. 604/317, 604/319, 360, 313, 540
See application file for complete search history.

(56) References Cited

U.S. PATENT DOCUMENTS

| | | | |
|---|---|---|---|
| 3,367,332 A | 2/1968 | Groves | |
| 3,486,504 A | 12/1969 | Austin, Jr. | |
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,266,545 A | 5/1981 | Moss | |
| 4,382,441 A | 5/1983 | Svedman | |

(Continued)

FOREIGN PATENT DOCUMENTS

DE    41 11 122 A1    4/1993

(Continued)

OTHER PUBLICATIONS

Meyer, M.D., et al., "In Surgery, Medicine and the Specialties A Manual of its Practical Application", Bier's Hyperemic Treatment, Second Revised Edition, W.B. Saunders Company, 1909.

(Continued)

*Primary Examiner* — Melanie Hand
(74) *Attorney, Agent, or Firm* — Eline Domingo, Esq.

(57) ABSTRACT

A system to promote the healing of an exuding wound includes a wound dressing, a subatmospheric pressure mechanism, and a collection canister. The wound dressing is dimensioned for positioning relative to a wound bed of a subject. The subatmospheric pressure mechanism includes a control unit disposed within a housing. The control unit includes a vacuum source associated with a vacuum port. The collection canister has an interior wall which defines an internal chamber. The internal chamber is in fluid communication with the vacuum source of the subatmospheric pressure mechanism through the vacuum port and with the wound dressing for collecting exudates removed for the wound bed under influence of the vacuum source. The canister including a baffle mechanism disposed within the internal chamber for dampening the movement of the collected exudates.

10 Claims, 6 Drawing Sheets

U.S. PATENT DOCUMENTS

| | | |
|---|---|---|
| 4,524,064 A | 6/1985 | Nambu |
| 4,743,232 A | 5/1988 | Kruger |
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,195,977 A | 3/1993 | Pollitt |
| 5,261,893 A | 11/1993 | Zamierowski |
| 5,263,922 A | 11/1993 | Sova et al. |
| 5,397,299 A * | 3/1995 | Karwoski et al. .............. 604/6.1 |
| D364,679 S | 11/1995 | Heaton et al. |
| 5,484,427 A | 1/1996 | Gibbons |
| 5,484,428 A * | 1/1996 | Drainville et al. ............ 604/319 |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,840,049 A | 11/1998 | Tumey et al. |
| 5,911,222 A | 6/1999 | Lawrence et al. |
| 5,944,703 A | 8/1999 | Dixon et al. |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 * | 4/2007 | Argenta et al. ............... 128/897 |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0143286 A1 | 10/2002 | Tumey |
| 2002/0151836 A1 | 10/2002 | Burden |
| 2003/0093041 A1 | 5/2003 | Risk, Jr. et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064132 A1 | 4/2004 | Boehringer et al. |
| 2004/0073151 A1 | 4/2004 | Weston |
| 2004/0093026 A1 | 5/2004 | Weidenhagen et al. |
| 2004/0122434 A1 | 6/2004 | Argenta et al. |
| 2004/0180093 A1 * | 9/2004 | Burton et al. ................. 424/489 |
| 2004/0193218 A1 | 9/2004 | Butler |
| 2004/0241213 A1 | 12/2004 | Bray |
| 2004/0243073 A1 | 12/2004 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1 | 11/2005 | Weston |
| 2005/0261643 A1 | 11/2005 | Bybordi et al. |
| 2006/0015087 A1 | 1/2006 | Risk, Jr. et al. |
| 2006/0025727 A1 | 2/2006 | Boehringer et al. |
| 2006/0039742 A1 | 2/2006 | Cable, Jr. et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |

| | | | |
|---|---|---|---|
| 2006/0149170 | A1 | 7/2006 | Boynton et al. |
| 2007/0005028 | A1 | 1/2007 | Risk, Jr. et al. |
| 2007/0014837 | A1 | 1/2007 | Johnson et al. |
| 2007/0021697 | A1 | 1/2007 | Ginther et al. |
| 2007/0027414 | A1 | 2/2007 | Hoffmann et al. |
| 2007/0032754 | A1 | 2/2007 | Walsh |
| 2007/0032755 | A1 | 2/2007 | Walsh |
| 2007/0032778 | A1 | 2/2007 | Heaton et al. |
| 2007/0055209 | A1 | 3/2007 | Patel et al. |
| 2007/0066946 | A1 | 3/2007 | Haggstrom et al. |
| 2007/0078366 | A1 | 4/2007 | Haggstrom et al. |
| 2007/0167927 | A1 | 7/2007 | Hunt et al. |
| 2007/0179460 | A1 | 8/2007 | Adahan |
| 2007/0185426 | A1 | 8/2007 | Ambrosio et al. |
| 2008/0071235 | A1 | 3/2008 | Locke et al. |
| 2008/0200857 | A1 | 8/2008 | Lawhorn |
| 2008/0200906 | A1 | 8/2008 | Sanders et al. |
| 2008/0208147 | A1 | 8/2008 | Argenta et al. |
| 2008/0234641 | A1 | 9/2008 | Locke et al. |

FOREIGN PATENT DOCUMENTS

| | | |
|---|---|---|
| DE | 295 04 378 U1 | 10/1995 |
| EP | 0 020 662 B1 | 7/1984 |
| EP | 0 358 302 | 3/1990 |
| EP | 0 853 950 B1 | 10/2002 |
| GB | 1 549 756 | 3/1977 |
| GB | 2 195 255 A | 4/1988 |
| GB | 2 235 877 A | 3/1991 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1990 |
| WO | 92/19313 | 11/1992 |
| WO | 96/05873 | 2/1996 |
| WO | 9605873 | 2/1996 |
| WO | 03057307 | 7/2003 |
| WO | 03101508 | 12/2003 |
| WO | 2005009488 | 2/2005 |

OTHER PUBLICATIONS

Jeter, Katherine F., et al., "Managing Draining Wounds and Fistulae: New and Established Methods", Chronic Wound Care, 1990, pp. 240-246.

Chariker, M. E. et al. (eds), "Effective Management of Incisional and Cutaneous Fistulae with Closed Suction Wound Drainage," Contemporary Surgery, vol. 34, Jun. 1989, pp. 59-63.

B.M. Kostiuchenok, et al., "The Vacuum Effect in the Surgical Treatment of Purulent Wounds," Russian Journal: Vestnik Khirurgii, Sep. 1986 (18-21).

Y.N. Usupov, et al., "Active Wound Drainage," Russian Journal: Vestnik Khirugii, Apr. 1987 (42-45).

Yu A. Davydov, et al., "Concepts for Clinical Biological Management of the Wound Process in the Treatment of Purulent Wounds Using Vacuum Therapy," Vestnik Khirugii, Feb. 1991, 132-135).

N.A. Bagautdinov (Kazan), "Variant of External Vacuum Aspiration in the Treatment of Purulent Diseases of Soft Tissues," UDC 616-002.36 (94-96).

Chardack, et al., "Experimental studies on Synthetic Substitutes for Skin and Their Use in the Treatment of Burns," vol. 155, No. 1 (128-136).

Gorica Zivadinovic, et al., "Vacuum Therapy in the Treatment of Peripheral Blood Vessels," Conference Papers of the 5th Timok Medical Days, Majdanpek, 1986 (161-164).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

W. Fleischmann, et al., Vacuum Sealing: Indication, Technique and Results, Emr J Orthop Surg Tramatol (1995) 5:37-40.

Sherry Stoll, "Energetic Remedies—Cupping: Healing Within a Vacuum," https://www.suite101.com/article.cfm/energetic)remedies/74531, Apr. 13, 2005.

Mulder, G.D, et al., "Clinicians' Pocket Guide to Chronic Wound Repair," Wound Healing Publications Second Edition, 1991.

Yu A. Davydov, et al., "Vacuum Therapy in the Treatment of Purulent Lactation Mastitis," Russian Journal: Vesnik Khirurgii, Sep. 1986 (66-70).

Yu A. Davydov, et al., "Bacteriological and Cytological Assessment of Vacuum Therapy of Purulent Wounds", Vestnik Khirurgii, Oct. 1988 (48-52).

W. Fleischmann, "Vacuum Sealing for Treatment of Problematical Wounds", University Surgical Clinic and Polyclinic—Accident Surgery Department, WundForum Spezial—IHW 94.

Göran Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Björn, et al., "Irrigation Treatment in Split-thickness Skin Grafting of Intractable Leg Ulcers," Scand J Plast Reconstr Surg 19: 211-213, 1985.

Paul Svedman, et al., "Staphylococcal Wound Infection in the Pig: Part I. Course," Annals of Plastic Surgery, vol. 23, No. 3, Sep. 1989 (212-218).

Paul Svedman, "A Dressing Allowing Continuous Treatment of a Biosurface," IRCS Medical Science: Biomedical Technology; Clinical Medicine; Surgery and Transplantation, 7, 221 (1979).

Paul Svedman, "Irrigation Treatment of Leg Ulcers," The Lancet, Sep. 3, 1983 (532-534).

H. Teder, et al., "Continuous Wound Irrigation in the Pig," Journal of Investigative Surgery, vol. 3 (399-407).

P. Svedman, "A Dressing System Providing Fluid Supply and Suction Drainage Used for Continuous or Intermittent Irrigation," Annals of Plastic Surgery, vol. 17, No. 2, Aug. 1986 (125-133).

Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

US 6,216,701, 04/2001, Heaton et al. (withdrawn)
US 7,186,244, 03/2007, Hunt et al. (withdrawn)

* cited by examiner

CANISTER FOR RECEIVING WOUND EXUDATE IN A NEGATIVE PRESSURE THERAPY SYSTEM

CROSS-REFERENCE TO RELATED APPLICATIONS

This application claims priority to, and the benefit of, U.S. Provisional Patent Application No. 61/143,449, filed Jan. 9, 2009, the entire contents of which are incorporated herein by reference.

BACKGROUND

1. Technical Field

The present disclosure relates to treating an open wound with a wound therapy system, and, more specifically, relates to a collection canister for a wound therapy system incorporating a baffle mechanism for minimizing flow of exudates within the canister thereby reducing the potential of spillage and communication of the exudates with operating components of the wound therapy system.

2. Description of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure wound therapy, also known as suction or vacuum therapy, has been used in treating and healing wounds. Application of negative pressure, e.g. reduced or subatmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure wound therapy provides for a wound to be covered to facilitate suction at the wound area. A conduit is introduced through the wound covering to provide fluid communication to an external vacuum source. Atmospheric gas, wound exudates, or other fluids may thus be drawn from the reservoir through the fluid conduit to stimulate healing of the wound. Exudates drawn from the reservoir may be deposited in a collection canister.

The collection canister fills with exudates and is typically changed every few days. The collected exudates are free to move around within the canister and may cause vacuum delay, such as by accidental contact with fluid sensors or other electronics of the system. Movement of the canister exudates may also cause spillage from the collection canister which may cause exposure to the collected wound exudates or affect disposal of the collection canister. Furthermore, varying species of bacteria and fungal isolates within the exudates grow and proliferate, which ultimately leads to foul odor. It would be advantageous to provide a collection canister with a baffle mechanism contained therein to reduce movement of exudates, to aid in disposal, and to limit any odor produced therein.

SUMMARY

Accordingly, a system to promote the healing of an exuding wound includes a wound dressing, a subatmospheric pressure mechanism, and a collection canister. The wound dressing is dimensioned for positioning relative to a wound bed of a subject. The subatmospheric pressure mechanism includes a control unit disposed within a housing. The control unit includes a vacuum source associated with a vacuum port. The collection canister has an interior wall which defines an internal chamber. The internal chamber is in fluid communication with the vacuum source of the subatmospheric pressure mechanism through the vacuum port and with the wound dressing for collecting exudates removed for the wound bed under influence of the vacuum source. The canister including a baffle mechanism disposed within the internal chamber for dampening the movement of the collected exudates.

The baffle mechanism increases the surface area within the canister. The additional surfaces serve to resist motion of the exudates upon movement of the canister and absorb the kinetic energy of the moving exudates. In embodiments, the baffle mechanism includes at least one baffle in the form of a permeable material segment. The material segment is treated with an antimicrobial agent to allow passage and treatment of the exudates therethrough for controlling the growth of microorganisms in the exudates. In embodiments, a plurality of baffles depends from the interior wall and within the internal chamber of the collection canister. Groups of baffles are similarly oriented within the canister to assist in impeding flow of the exudates. In yet other embodiments, a fluid solidifier is disposed in a select portion of the canister and maintained in place via a water soluble adhesive for dampening movement of exudates by consolidating the exudates into a substantially non-flowable state.

BRIEF DESCRIPTION OF THE DRAWINGS

Various embodiments of the wound therapy system of the present disclosure are described herein with reference to the drawings wherein.

DESCRIPTION OF THE EMBODIMENTS

The wound therapy system of the present disclosure promotes healing of a wound via the use of a wound dressing, a subatmospheric pressure mechanism, and a collection canister. Generally, the subatmospheric pressure mechanism applies subatmospheric pressure to the wound to effectively remove wound fluids or exudates captured within the boundary of the composite wound dressing, and to increase blood flow to the wound bed and enhance cellular stimulation of epithelial and subcutaneous tissue. The wound therapy system may be entirely portable, i.e., it may be worn or carried by the subject such that the subject may be completely ambulatory during the therapy period. The wound therapy system including the subatmospheric pressure mechanism and components thereof may be entirely reusable or may be entirely disposable after a predetermined period of use or may be individually disposable whereby some of the components are reused for a subsequent therapy application.

The wound therapy system of the present disclosure promotes healing of a wound in conjunction with subatmospheric negative pressure therapy. The system may incorporate a variety of wound dressings, subatmospheric pressure sources and pumps, and collection canisters. The attached figures illustrate exemplary embodiments of the present disclosure and are referenced to describe the embodiments depicted therein. Hereinafter, the disclosure will be described by explaining the figures wherein like reference numerals represent like parts throughout the several views.

Figure 1:
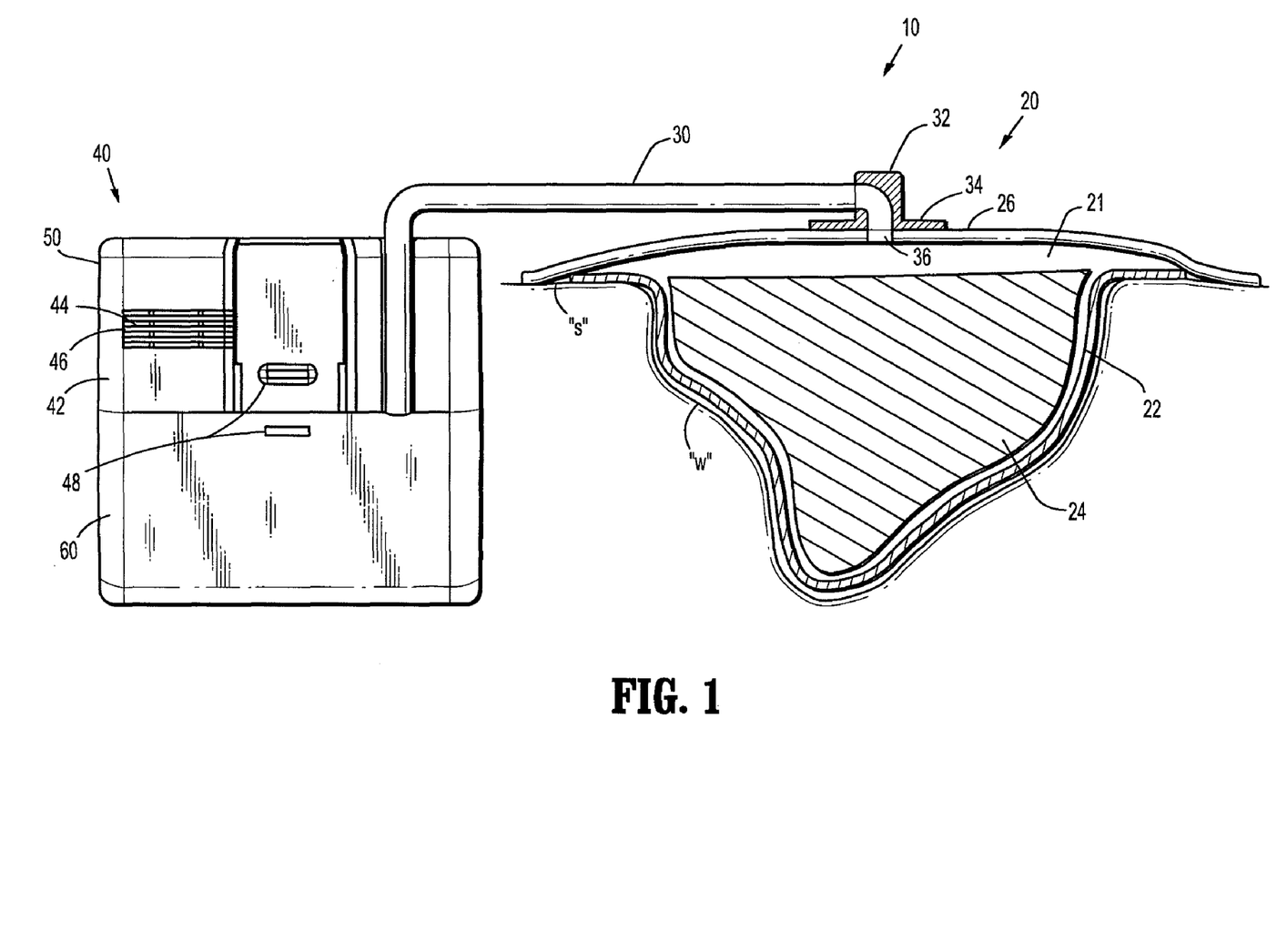
FIG. 1 is a view in partial cross-section of a wound therapy system of the present disclosure illustrating the wound dressing, the subatmospheric pressure mechanism, and the collection canister.

Referring initially to FIG. 1, the wound therapy system 10 according to the present disclosure is illustrated for use on a wound "w" surrounded by healthy skin "s." Wound therapy system 10 includes composite wound dressing 20, subatmospheric pressure mechanism 40, and collection canister 60 in fluid communication with the wound dressing 20 through conduit 30.

Wound dressing 20 is positioned relative to the wound "w" to define a reservoir 21 in which a negative pressure appropriate to stimulate healing may be maintained. Wound dressing 20 may include several components, namely, wound contact layer or member 22, a wound packing member or filler 24 supported by the contact member 22 and outer layer or cover member 26. Wound contact member 22 is adapted to substantially conform to the topography of a wound bed "w." Wound contact member 22 may be substantially porous or perforated to permit exudates to pass from the wound bed "w" through the wound contact member 22. The passage of wound exudates through the wound contact member 22 may be unidirectional such that wound exudates do not flow back to the wound bed "w." Unidirectional flow may be encouraged by directional apertures formed in contact member 108, lamination of materials having absorption properties differing from those of contact member 22, or by selection of materials that promote directional flow. A non-adherent material may be selected such that contact member 22 does not tend to cling to wound bed "w" or surrounding material when it is removed. Exemplary materials that may be used as contact member 22 are sold under the trademarks XEROFORM® and CURITY®, offered by Tyco Healthcare Group LP (d/b/a Covidien).

Wound packing member 24 of wound dressing 20 is intended to transfer wound fluid and exudates. Wound packing member 24 is conformable to assume the shape of any wound bed "w" and may be packed up to the level of healthy skin "s." Wound packing member 24 may be pre-formed in any shape and size or may be custom fit by cutting the packing member 24 to a desired shape and/or size. Wound packing member 24 may be treated with agents to promote healing of the wound, such as polyhexamethylene biguanide (PHMB) to decrease the incidence of infection, or other substances having clinical use, such as other medicaments. Suitable materials for wound packing member 24 are sold under the trademarks KERLIX®, EXCILON®, and WEBRIL®, all by Tyco Healthcare Group LP (d/b/a Covidien).

Outer member or wound covering 26 encompasses the perimeter of the wound dressing 20 to surround wound bed "w" and to provide a liquid and/or fluid tight seal around the perimeter "p" of the wound bed "w." For instance, the sealing mechanism may be any adhesive bonded to the perimeter of wound covering 26. One exemplary material that may be used as an adhesive dressing is sold under the trademark CURAFORM® Island Dressing by Tyco Healthcare Group LP (d/b/a Covidien). Thus, wound covering 26 may act as both a microbial barrier and a fluid barrier to prevent contaminants from entering wound bed "w" and for maintaining the integrity thereof.

Wound covering 26 is typically a flexible material, e.g., resilient or elastomeric, that seals the top of wound dressing 20 to prevent passage of liquids, fluids, and/or contaminants to and from the wound dressing 20. Wound covering 26 may be formed from a moisture vapor permeable membrane to promote the exchange of oxygen moisture between the wound bed "w" and atmosphere. A membrane that provides a sufficient moisture vapor transmission rate is a transparent membrane sold under the trademark POLYSKIN® II by Tyco Healthcare Group LP (d/b/a Covidien). A transparent membrane permits an assessment of wound conditions without requiring removal of the wound covering 26. Alternatively, wound covering 26 may comprise an impermeable membrane or a substantially rigid membrane.

Wound covering 26 may include a port or connector 32 in fluid communication with the interior of wound dressing 20 to facilitate connection of wound dressing 20 to conduit or tubing 30. Conduit 30 defines a fluid flow path leading through wound therapy system 10. Connector 32 may be configured as a rigid or flexible, low-profile component, and may be adapted to receive conduit 30 in a releasable and fluid tight manner. An adhesive on the underside of flange 34 of connector 32 may provide a mechanism for affixing the conduit 30 to the wound dressing 20 or alternatively, flange 34 may be positioned within reservoir 21 such that an adhesive on an upper side of the flange 34 affixes the conduit 30. However it is affixed to wound dressing 20, a hollow interior 36 of connector 32 provides fluid communication between conduit 30 and the interior of wound dressing 20, such as reservoir 21.

Connector 32 may have a valve (not shown) built therein or in line with conduit 30, e.g., a one-way valve to permit exudates to flow in one direction only, i.e., away from wound dressing 20 toward subatmospheric pressure mechanism 40. Connector 32 may be provided as a pre-affixed component of wound dressing 20, as a component of conduit 30 or entirely separate and connected thereto by conventional means. Alternatively, connector 32 may be eliminated if other provisions are made for providing fluid communication between wound dressing 20 and conduit 30.

Conduit 30 extends from subatmospheric pressure mechanism 40 to provide fluid communication between the interior of the wound dressing 20 and subatmospheric pressure mechanism 40. Any suitable conduit may be used including those fabricated from flexible elastomeric or polymeric materials. Conduit 30 may connect to subatmospheric pressure mechanism 40 or other system components by conventional air tight means such as friction fit, bayonet coupling, or barbed connectors. The conduit connections may be made permanent, or alternatively a quick-disconnect or other releasable means may be used to provide some adjustment flexibility to the apparatus.

Figure 2:
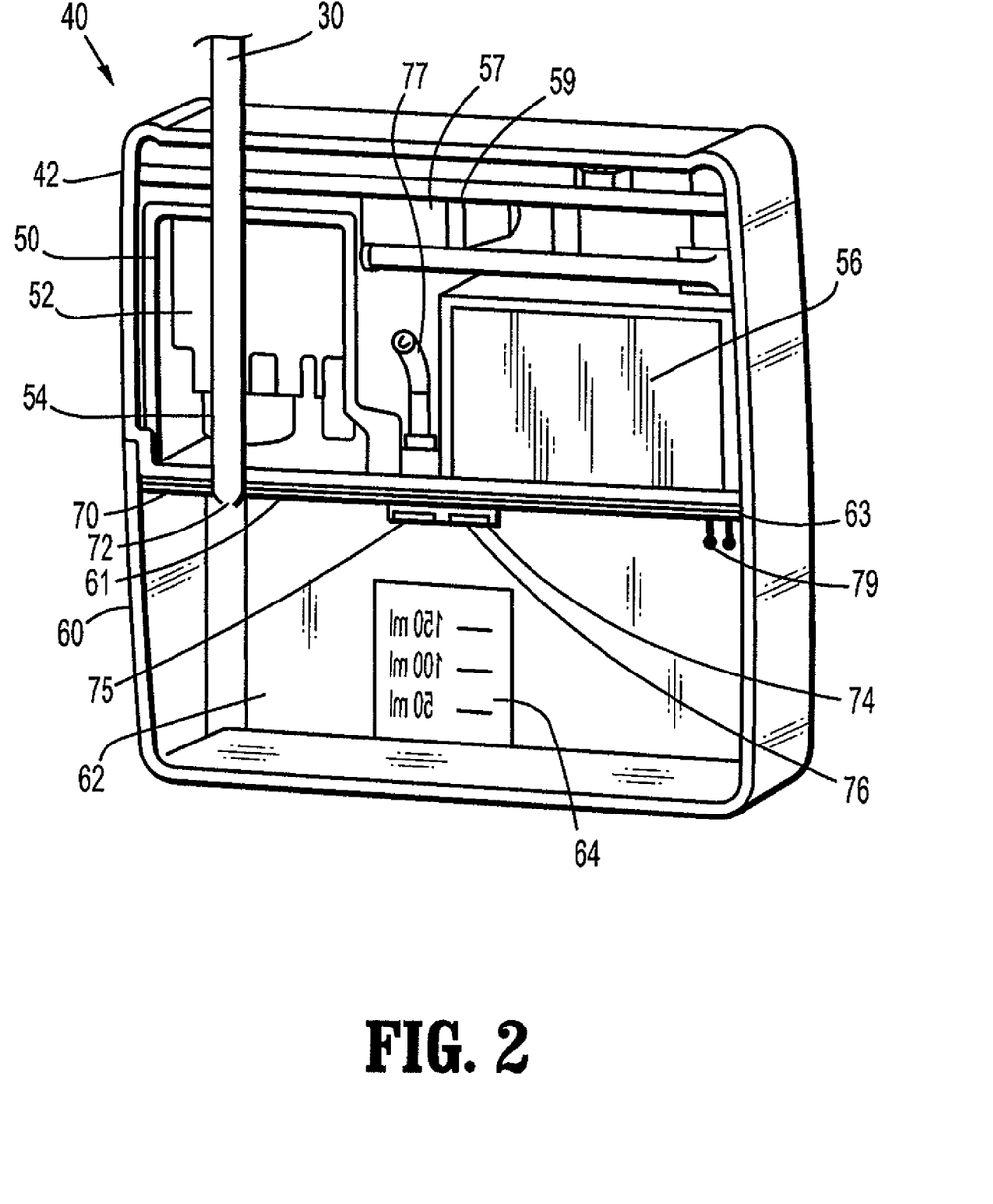
FIG. 2 is a perspective cross-sectional view of an embodiment of a subatmospheric pressure mechanism and a canister of the wound therapy system of the present disclosure.

Referring now to FIG. 2, in conjunction with FIG. 1, subatmospheric pressure mechanism 40 and collection canister 60 will be discussed. Subatmospheric pressure mechanism 40 includes housing 42 and control unit 50 disposed within the housing 42. Housing 42 may be any suitable rigid member which may be adapted for donning by the subject. Control unit 50 may incorporate vacuum source or pump 52, actuator or motor 54 for activating the vacuum source 52, and power source 56. Vacuum source or pump 52 generates or otherwise provides negative pressure to wound therapy system 10. Vacuum source or pump 52 may be a pump of the diaphragmatic, peristaltic or bellows type or the like, in which the moving part(s) draw exudates out of the wound bed "w" into the wound dressing 20 by creating areas or zones of decreased pressure e.g., vacuum zones with the wound dressing 20 appropriate to stimulate healing of the wound. This area of decreased pressure may communicate with the wound bed "w" to facilitate removal of the fluids therefrom and into packing member 24.

Vacuum source or pump 52 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg and about 125 mmHg, or between about 30 mmHg and 80 mmHg. Vacuum source or pump 52 is actuated by actuator 54 which may be any means known by those skilled in the art, including, for example, AC motors, DC motors, voice coil actuators, solenoids, and the like. Actuator 54 may be incorporated within pump 52.

Power source 56 may be disposed within housing 42 or separately mountable to housing 42. A suitable power source 56 includes alkaline batteries, wet cell batteries, dry cell batteries, nickel cadmium batteries, solar generated means, lithium batteries, NiMH batteries (nickel metal hydride) each of which may be of the disposable or rechargeable variety.

Subatmospheric pressure mechanism 40 may also include a pressure transducer 57 which may be attached to a printed circuit board (PCB) 59. Within the PCB 59 is software or circuitry that powers the pressure transducer 57 and receives its pressure signals (i.e., electrical signals indicative of the negative pressure being measured).

Housing 42 may include vent portal 44 configured to vent exhaust air from vacuum source or pump 52 through an exhaust port (not shown). Vent portal 44 extends from housing 42 and may be directly connected to vacuum source 52. It is also envisioned that vent portal 44 may exhaust air from within housing 42 rather than directly from vacuum source 52. A filter 46 may extend across vent portal 44. Filter 46 may be a bacterial and/or odor control filter to prevent emission of bacteria and/or odors from housing 42.

Collection canister 60 collects exudates "e" removed from the wound bed "w" during therapy through conduit or tubing 30. Collection canister 60 is associated with housing 42 and may be incorporated within the housing 42 or releasably connected to the housing 42 by conventional means. Housing 42 and collection canister 60 may be releasably coupled via mating members 48. Mechanisms for selective coupling and decoupling of housing 42 and collection canister 60 include fasteners, latches, clips, straps, bayonet mounts, magnetic couplings, and other devices for selective mating of housing 42 and collection canister 60.

Collection canister 60 may comprise any container suitable for containing wound fluids and is substantially rigid defining an internal chamber 62 in fluid communication with tubing 30. In the alternative, collection canister 60 may be relatively flexible. In embodiments, at least a portion of collection canister 60 may be transparent to assist in evaluating the color, quality, or quantity of wound exudates. A transparent or partially transparent window 64 may thus assist in determining the remaining capacity of the canister 60 or when the canister 60 should be replaced.

Collection canister 60 includes fluid inlet 72 and suction port 74. Collection canister 60 may also include pressure transducer port 75 and/or fill sensor 79. Fluid inlet 72 is configured to operably engage conduit 30. Fluid inlet 72 may be connectable with conduit 30 by conventional air and fluid tight means, such as those described above and terminates within internal chamber 62 to deposit fluids and exudates conveyed by conduit 30 into internal chamber 62. In embodiments, fluid inlet 72 may contain a luer lock or other connector within the purview of those skilled in the art to secure the end of conduit 30 with the fluid inlet 72. It is envisioned that fluid inlet 72 is configured to receive a cap or a tubing clamp in order to prevent leakage of exudates and odor from internal chamber 62 of collection canister 60 when housing 42 is separated from the canister 60.

Suction port 74 of collection canister 60 is in fluid communication with vacuum source or pump 52 of subatmospheric pressure mechanism 40. Pump 52 creates a vacuum within internal chamber 62 of collection canister 60 by drawing air through suction port 74. A filter 76, such as a hydrophobic membrane or baffling to prevent exudates from being aspirated into pump 52, may be disposed within suction port 74. Alternatively, filter 76 may be disposed adjacent to suction port 74 such that suction port 74 passes air between vacuum source 52 and canister 60 through filter 76 while keeping the contents from reaching the vacuum pump 52 or other components of control unit 50.

The hydrophilic nature of the filter 76 allows the collection canister 60 to be oriented in a way other than with the pump 52 above the canister 60, such as on the side of the canister 60 or tipped, without exudates in the canister 60 being aspirated into pump 52. Some portion of the surface of filter 76 remains uncovered, thereby allowing continued flow of air to vacuum pump 52. Filter 76 may include charcoal or other odor absorbing materials and may prevent the passage of bacteria.

Pressure transducer port 75 is in fluid communication with pressure transducer 57 through tube 77 and permits the monitoring of pressure levels within internal chamber 62 of collection canister 60. Filter 76 may be disposed between pressure transducer port 75 and internal chamber 62 of collection canister 60 to prevent the migration of fluids or exudates into the pressure transducer port 75 and the pressure transducer 57.

Fill sensor 79 is disposed within collection canister 60 at a pre-determined height or level within the canister 60 corresponding to a targeted volume of fluid or exudates accumulation within the canister 60, such as at a position corresponding to a maximum fill volume of the canister 60. Fill sensor 79 incorporates electrically conductive contacts which are connected to an indicator which generates an alert or signal that the canister 60 is full.

In embodiments, collection canister 60 includes canister insert 61. Canister insert 61 is dimensioned to fill the opening of canister 60 and to be placed within internal chamber 62 of canister 60 until it engages a lip 63 around at least a portion of the peripheral inner edge of canister 60 or frictionally engages the inner walls of the canister in a fluid tight, yet releasable manner. Canister insert 61 may include the fluid inlet 72, suction port 74, pressure transducer port 75, and/or filter 76. Alternatively, the components discussed above may be maintained within a top cover portion of collection canister 60 or may be maintained within a lower bottom portion of the housing 42 of subatmospheric pressure mechanism 40.

Collection canister 60 includes baffle mechanism 100 disposed within internal chamber 62 of the canister 60. Baffle mechanism 100 includes components for dampening exudates movement which may occur from user movement, such as bending or otherwise reorienting the body, or through waves of "sloshing" caused by cyclical movements, such as walking. The baffle mechanism 100 is effective against fluid movement without affecting the collection capability of canister 60.

The baffle mechanism 100 may include three dimensional structures or baffles 110 disposed freely within the canister 60 or formed as part of, or attached to, the collection canister 60. The baffle mechanism 100 provides additional surface area within collection canister 60 thereby dividing the surface area of the exudates within the canister 60 into smaller areas. The additional surfaces resist motion, such as wave action or liquid sloshing, of the exudates. The additional surfaces also serve to dampen the movement of the exudates in the canister thereby at least partially absorbing the kinetic energy of the exudates.

Figure 3:
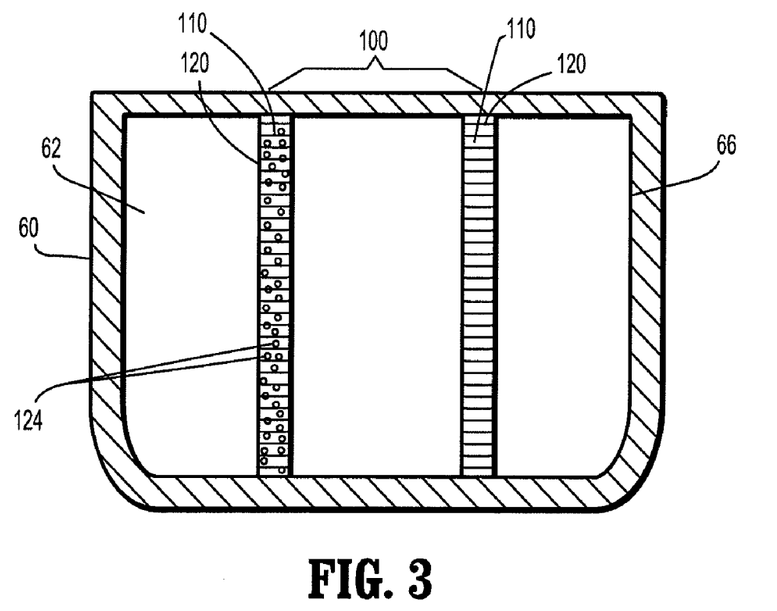
FIG. 3 is a cross-sectional view of a collection canister having a baffle mechanism including an antimicrobial treated material segment contained therein in accordance with the present disclosure.
Figure 4:
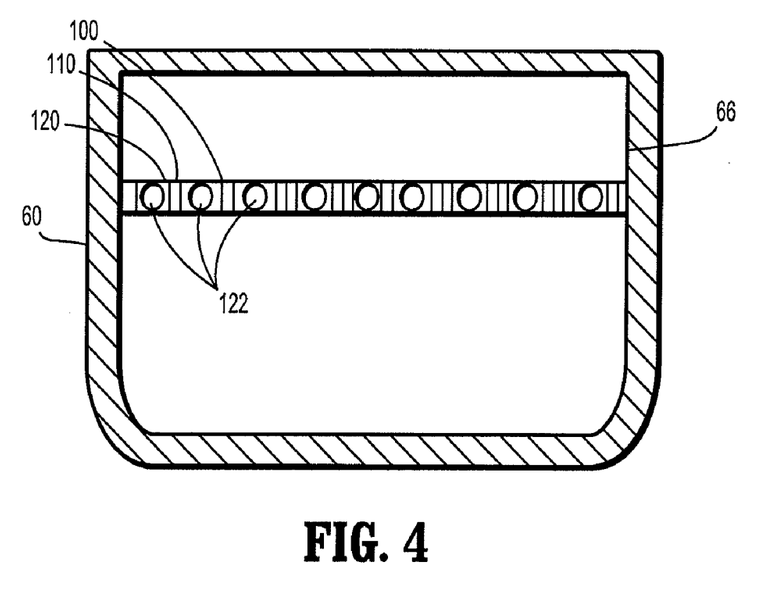
FIG. 4 is a cross-sectional view of another embodiment of a collection canister including an antimicrobial treated material segment contained therein.
Figure 5A:
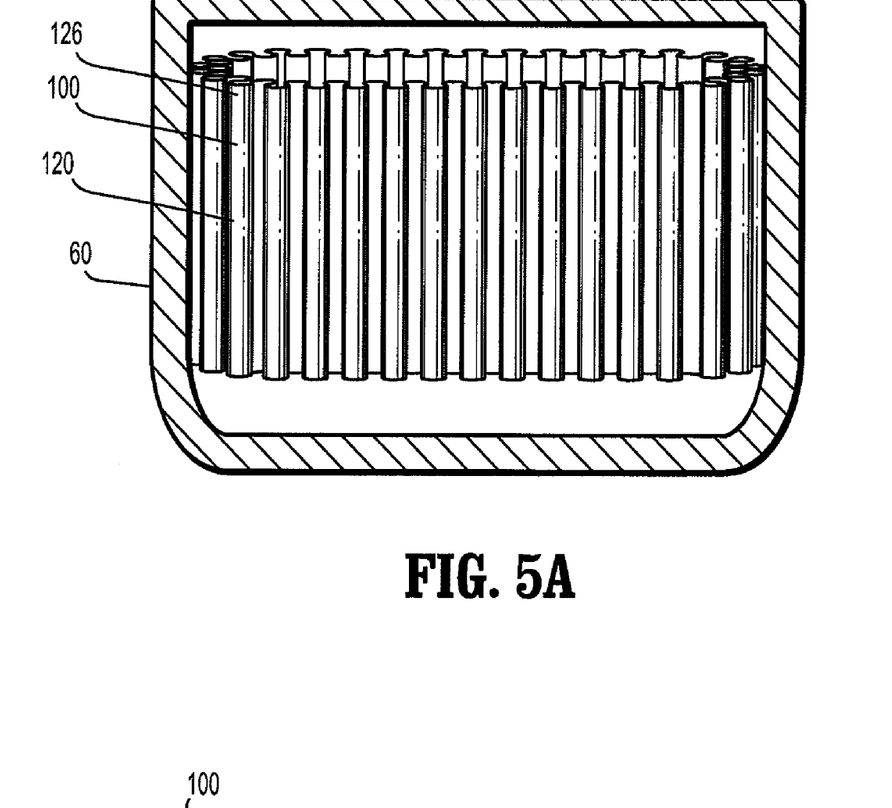
FIGS. 5A-5B are side and top views of another embodiment of an antimicrobial treated material segment of a baffle mechanism of the collection canister of the present disclosure.
Figure 5B:
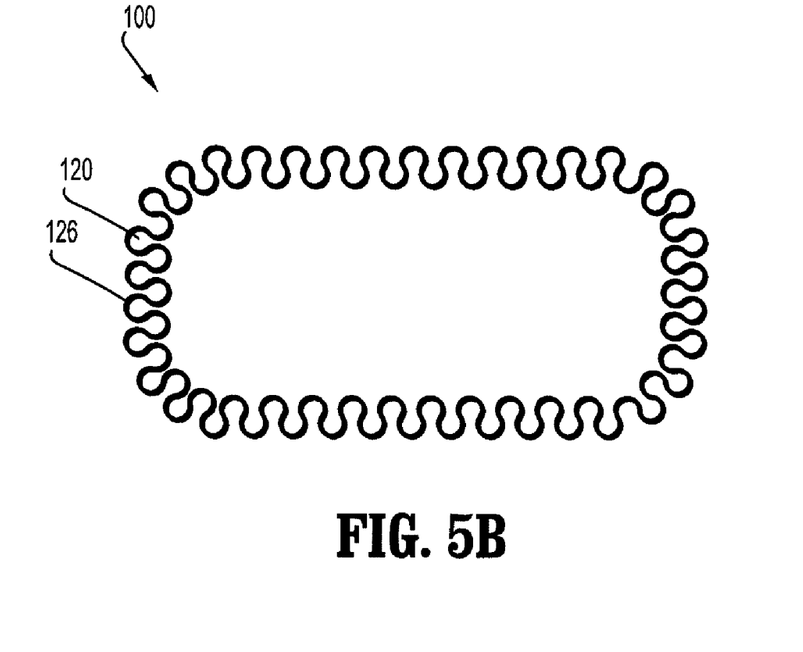

In an embodiment of the baffle mechanism of the present disclosure depicted in FIGS. 3-5, baffle mechanism 100 includes at least one baffle 110 fabricated from a material segment 120. Material segment 120 may be formed from woven or nonwoven materials in the form of a knit, weave, mesh, sheet, web, or other construct within the purview of those skilled in the art that has been formed by mechanically, chemically, or thermally bonding of the material. The nonwoven material may have a structure of fibers or threads which are interlaid or bonded in a random or systematic manner through a variety of processes, such as, for example, melt-blowing or spunbonding. The fibers may be natural or man-made fibers, such as regenerated or synthetic fibers. Exemplary materials include, but are not limited to, polypropylene, high and low density polyethylene, ethylene copolymers, propylene copolymers, polyvinyl chloride, polyesters, polyamides, polyfluorocarbons, polyurethane, polystyrene, polyvinyl alcohol, caprolactams, cellulosic and acrylic resins, and bicomponents and/or blends thereof.

Material segment 120 may also be hydrophobic so that it will not absorb wound exudates as it is collected in canister 60. Hydrophobic materials include, for example, polyolefins and polyesters, as listed above.

The material segment 120 may have a low apparent density of less than about 0.1 grams per cubic centimeter. The material segment 120 may also have a relatively high fiber diameter. In embodiments, the fiber diameter is about 1 micron to about 14 microns. In some embodiments, the fiber diameter is greater than 15 microns.

Material segment 120 may also be permeable to allow for flow of exudates, gases and/or liquids, therethrough. Material segment 120 may include apertures 122, as illustrated in FIG. 4, to facilitate the passage of fluids, such as gases and liquids, therethrough. Material segment 120 may be disposed only with the upper portion of canister 60 thereby allowing for relatively free movement of exudates within the canister bottom.

In embodiments, material segment 120 is treated with an antimicrobial agent 124. The permeable or porous nature of the material segment 120 allows exudates to pass through and be treated by the antimicrobial agent 124. For example, the antimicrobial agent may be imparted to the material segment 120, or to the individual fibers thereof, by any method within the purview of those skilled in the art, such as by distributing the agent throughout the material or by providing a coating thereon. The antimicrobial agent may then be released from the material segment 120 upon contact with moisture.

Antimicrobial agents include compounds that kill microorganisms and/or prevent or inhibit their growth or production. Antimicrobials may be antibiotics, antiseptics, anti-fungals, and combinations thereof. The antimicrobial agents utilized within the present disclosure include triclosan, also known as 2,4,4'-trichloro-2'-hydroxydiphenyl ether, the biguanides, especially chlorhexidine and its salts, including chlorhexidine acetate, chlorhexidine gluconate, chlorhexidine digluconate, chlorhexidine hydrochloride, and chlorhexidine sulfate, silver and its salts, including silver acetate, silver benzoate, silver carbonate, silver citrate, silver chloride, silver iodate, silver iodide, silver lactate, silver laurate, silver nitrate, silver oxide, silver palmitate, silver zeolite, silver protein, and silver sulfadiazine, polymyxin, tetracycline, aminoglycosides, such as tobramycin and gentamicin, rifampician, bacitracin, neomycin, chloramphenical, miconazole, tolnaftate, quinolones such as oxolinic acid, norfloxacin, nalidix acid, pefloxacin, enoxacin and ciprofloxacin, penicillins such as ampicillin, amoxicillin, oxacillan, and piracil, cephalosporins, vancomycin, and combinations of any of the above antimicrobials.

In other embodiments, suitable biguanides which may be utilized as antimicrobial agents include hexamethylene biguanides, oligo-hexamethyl biguanides, and/or water-soluble polymers, e.g. polyhexamethylene biguanide (PHMB), or a suitable salt thereof. Any polymeric biguanide within the purview of those skilled in the art may be used herein.

Polymeric biguanides useful herein may include oligo- or poly alkylene biguanides or salts thereof or mixtures thereof. Suitable salts include water-soluble salts with inorganic or organic acids, for example hydrochlorides, hydrobromides, borates, acetates, gluconates, sulfonates, maleates, ascorbates, stearates, tartrates or citrates. Examples of specific polymeric biguanides and salts thereof which may be utilized as antimicrobials include polyhexamethylene biguanide, polyhexamethylene biguanide hydrochloride, polyhexamethylene biguanide hydrobromide, polyhexamethylene biguanide borate, polyhexamethylene biguanide acetate, polyhexamethylene biguanide gluconate, polyhexamethylene biguanide sulfonate, polyhexamethylene biguanide maleate, polyhexamethylene biguanide ascorbate, polyhexamethylene biguanide stearate, polyhexamethylene biguanide tartrate, polyhexamethylene biguanide citrate, and combinations thereof.

In some embodiments, PHMB hydrochloride, PHMB stearate, and the like may be utilized. Polyhexamethylene biguanide hydrochloride is a polymeric material that is commercially available as COSMOCIL® CQ from ARCH® Biocides, a division of Arch Chemicals, Inc. (Norwalk, Conn.).

PHMB hydrochloride is active against a wide range of microorganisms, it has very low mammalian toxicity, and it is chemically stable. Polyhexamethylene biguanide hydrochloride is also referred to as polyaminopropyl biguanide by the Cosmetic Toiletries and Fragrances Association (CTFA).

Anti-fungals which may be utilized with the present disclosure include azoles, polyenes, allylamines, and echinocandins. Examples include miconazole, ketoazole, econazole, itraconazole, sertaconazole, fluconazole, voriconazole, clioquinol, bifoconazole, terconazole, butoconazole, tioconazole, oxiconazole, sulconazole, saperconazole, clotrimazole, anidulafungin, caspofungin, micafungin, undecylenic acid, haloprogin, flucytosine, butenafine, tolnaftate, nystatin, ciclopirox, benzoic acid, olamin, terbinafine, amorolfine, naftifine, elubiol, griseofulvin, salts and/or combinations thereof.

Natural antimicrobial agents may also be utilized in the present disclosure. Natural antimicrobial agents include cinnamon oil, cinnamaldehyde, lemongrass oil, clove oil, saw palmetto extract, thyme oil white, thyme oil red, thymol, tea tree oil, *pinus pinaster* bark extract, rosemary leaf extract, grape seed extract, and betel oil.

In some illustrative embodiments of the present disclosure colorants, emulsifiers, surfactants, and color stabilizers that are will known within the art are added to the material segment 120. The colorants, in the form of dyes or pigments, aid in reducing shelf life discoloration or discoloration due to the effects of sterilization. The addition of emulsifiers and surfactants aid in surface wettability. Color stabilizers are sometimes added when the antimicrobial is a silver salt.

Material segment 120 may be formed as part of collection canister 60, may be an attachment thereto, or may be a removable insert adapted for positioning within collection canister 60. As such, material segment 120 may be any shape and size and come in a variety of configurations, such as a straight, pleated, ribboned, or random design. Additionally, one or more of the same or different material may be connected together to form material segment 120. Further, material segment 120 may be produced by any number of manufacturing techniques. Material segment 120 may, for example, be heat formed, cut, stamped, patterned, pressed, extruded, or molded into a desired configuration.

The material segment 120 may be anchored to opposing sides of interior wall 66 of canister 60 as illustrated in FIGS. 3-4, or connected between any two points within canister 60. Any number of material segments 120 may be included therein. Material segment 120 may be attached in any manner, including, gluing, melting, welding, riveting, stapling, and other adhesion methods within the purview of those skilled in the art.

Alternatively, if the material segment 120 is configured as an insert 126, as illustrated in FIGS. 5A-5B, the material segment must be of a sufficient rigidity, thickness, or size to maintain its form within canister 60. Further, as illustrated, the insert 126 may be shaped to be circumferentially compressed within canister 60. Alternatively, insert 126 may be freely disposed within canister 60 to move with the exudates. Upon movement of canister 60, kinetic energy of the exudates may be uniformly imparted on the mutually moving insert 126.

Figure 6:
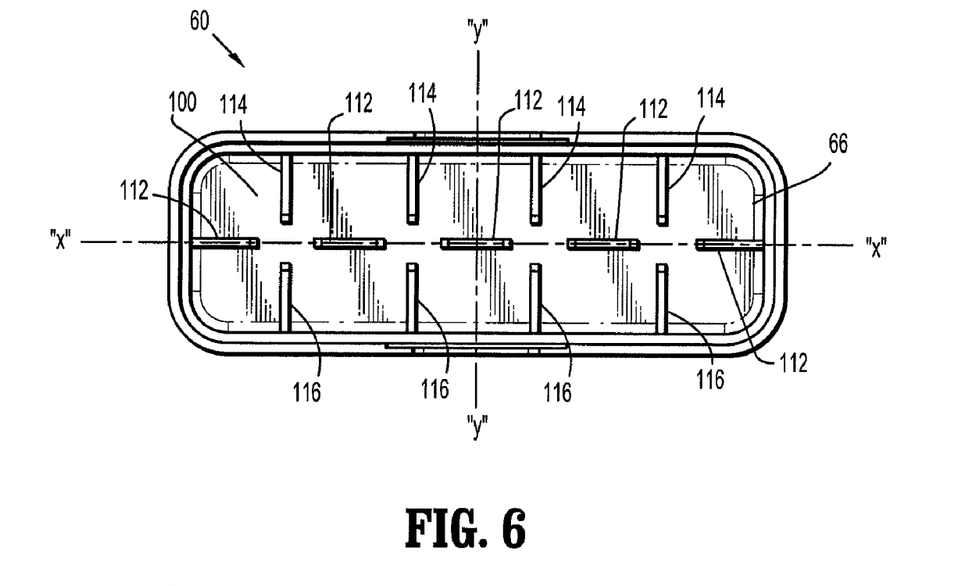
FIG. 6 is a top view of an embodiment of a collection canister having a baffle mechanism including a plurality of baffles contained therein in accordance with the present disclosure.
Figure 7:
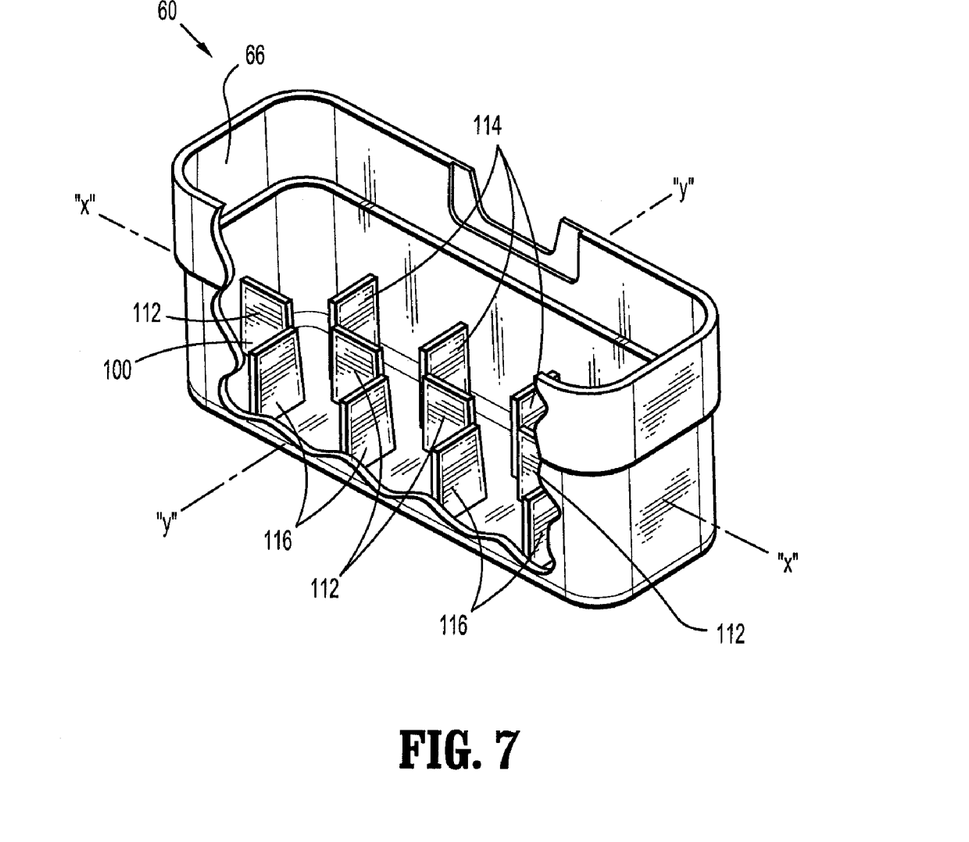
FIG. 7 is a side perspective view in partial cross-section of the collection canister of FIG. 6.

In another embodiment of the baffle mechanism 100 of the present disclosure as depicted in FIGS. 6-7, the baffle mechanism 100 includes a plurality of baffles depending from the interior wall 66 of the collection canister 60. The baffles may be material segments 120 as described above which have been treated with antimicrobial agent(s). The baffles may also or alternatively be treated with other bioactive agents, coated with a polymeric material to impart desired physical characteristics such as permeability and flexibility, or combinations thereof. Moreover, the plurality of baffles 110 may be fabricated from the same or different materials and accordingly, have uniform or varying properties.

The bioactive agent may be any substance or mixture of substances that have clinical use. Consequently, bioactive agents may or may not have pharmacological activity per se, e.g., a dye or fragrance. Alternatively, a bioactive agent could be any agent that provides a therapeutic or prophylactic effect to the collected wound exudates, a compound that affects or participates in tissue growth, cell growth, or cell differentiation, a compound that may be able to invoke a biological action, or could play any other role in one or more biological processes. It is envisioned that the bioactive agent may be treated on the baffle in any suitable form of matter, e.g., powders, gels, or films, by any suitable method for distributing the agent throughout the material or providing a coating thereon, including for example, spraying, dipping, brushing, and melting of the bioagent onto the baffle.

Examples of classes of bioactive agents which may be utilized in accordance with the present disclosure include antimicrobials, antibacterials, antibiotics, anti-virals, and anti-fungals for controlling the growth of microorganisms in the collected wound exudates. The bioactive agent may also be a fragrance, such as an odor control scent powder, for controlling the odor of the exudates. It is also intended that combinations of bioactive agents may be used.

Collection canister 60 includes longitudinal axis "x" and orthogonal axis "y" which is substantially perpendicular to longitudinal axis "x." Baffles depend from interior wall 66 of the canister 60 and may be positioned in any orientation relative to the longitudinal axis "x" and the orthogonal axis "y." For example, some or all baffles may be oriented parallel to the longitudinal axis "x," the orthogonal axis "y," and/or transverse to both axes.

As illustrated in the current embodiment, canister 60 includes groups of baffles, each group including similarly or identically oriented baffles within canister 60. A first group includes one or more baffles 112 which are oriented in parallel and spaced relation with respect to the longitudinal axis "x". In embodiments, baffles 112 are coincident with axis "x." A second group includes one or more baffles 114 which are oriented in transverse and spaced relation with respect to the longitudinal axis "x." Baffles 114 may be positioned at any angle that is crosswise to the longitudinal axis, in embodiments, the baffles 114 are perpendicular to the longitudinal axis and are parallel to the orthogonal axis "y." A third group includes one or more baffles 116 which are also arranged in space relation with respect to the longitudinal axis. Baffles 116 may be arranged in a general diametrical opposed relation with respect to baffles 114.

The groups of baffles 112, 114, 116 define a serpenditious path along at least the lower section of canister 60 through which the exudates must navigate during tilting and/or maneuvering of the canister 60, which occurs during ambulatory movement of the subject. In addition, the arrangement of baffles 112, 114, 116 substantially increases the surface area or contact area of the lower section of canister 60 with the exudate thereby increasing the absorption of the kinetic energy of the moving exudates.

Figure 8:
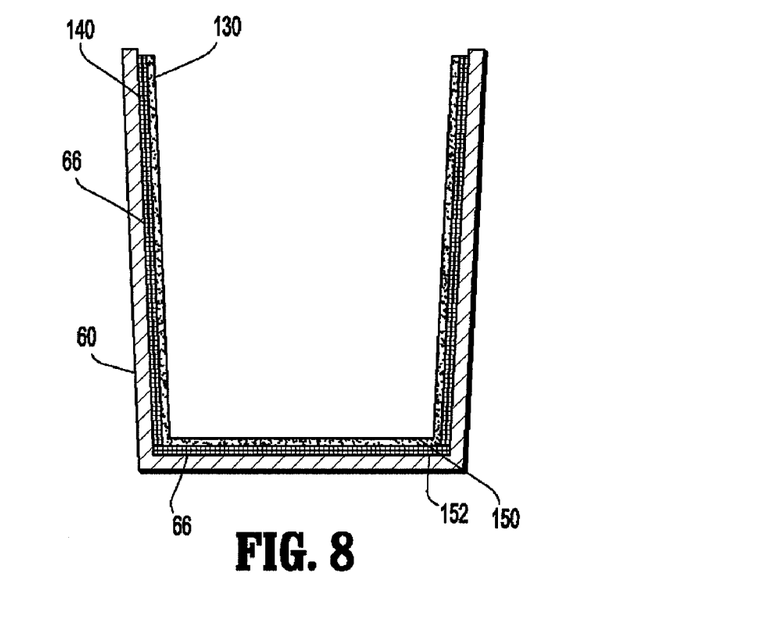
FIG. 8 is a side cross-sectional view of an embodiment of a collection canister having a baffle mechanism including a fluid solidifier coated therein in accordance with the present disclosure.
Figure 9:
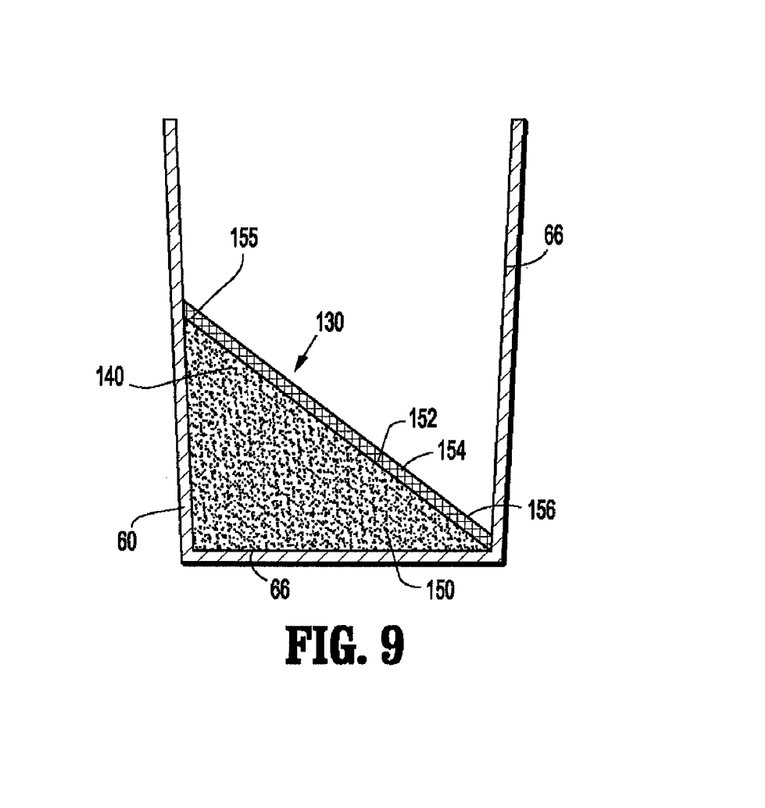
FIG. 9 is a side cross-sectional view of another embodiment of a collection canister including a fluid solidifier contained therein.

Turning now to FIGS. 8-9, an alternative embodiment of the baffle mechanism 130 of the present disclosure is illustrated. Baffle mechanism 130 includes a baffle 140 in the form of a fluid solidifier 150 which allows collected wound fluid and exudates to gel or solidify thereby consolidating and containing the exudates in the collection canister 60. The fluid solidifier 150 alters the state of the fluids and exudates to a substantially non-flowable state. By rendering the collected exudates in a non-flowable state, the collection canister 60 may be more portable by dampening exudates movement within the canister 60. Consolidation may also help avoid vacuum delay by minimizing clogging of filter 76, preventing inadvertent contact of the exudates with the pressure transducer port 75, and unintentional triggering of fill sensor 79.

Fluid solidifier 150 may be one or a mixture of absorbents having the same or different bulk densities. In embodiments, the fluid solidifier 150 is in powder form. The absorbents may also have the same or different absorbing capacity. The absorbing capacity may be influenced by the shape of the absorbent and the wettability of the absorbent by the wound exudates, among other things. The rate of absorption may be dependent upon the ratio of the amount of absorbent used per volume of exudates.

The fluid solidifier 150 may be any commercially available solidifier agent such as Solidifier manufactured by DeRoyal Industries, Absorb-O-Gel™ available from Pioneer Medical, Aqua-Keep™ manufactured by Sumitomo and available from Absorbent Technologies, Norscoryl™ S-35 manufactured by Emerging Technologies, Inc. and available through The Chemical Company, Medigel™ 300 available from BASF, Flosorb™ 60 available from Chemtall, Inc., and SA60N type II, available from Absorbent Technologies. In embodiments the fluid solidifier 150 may be mixed with a bioactive agent as described above.

Fluid solidifier 150 may be disposed in any portion of collection canister 60. As illustrated in the embodiment of FIG. 8, the fluid solidifier 150 is applied to the walls 66 of the canister 60 by use of a water soluble adhesive 152. The water soluble adhesive 152 may be any adhesive that allows for temporary bonding of the fluid solidifier 150 until it is contacted with a fluid. The water soluble adhesive 152 is of sufficient adhesive strength to maintain the fluid solidifier 150 on the walls 66 of the canister 60 when dry. The adhesive 152 can be separated from the wall 66 once wet. Accordingly, after the wound fluid or exudates contacts a portion of wall 66, the adhesive 152 releases the fluid solidifier 150 from the wall 66.

The water soluble adhesive 152 may be sprayed or coated onto the walls 66 of the canister 60. The fluid solidifier 150 may then be applied thereon in powder or other form by any suitable technique. This configuration will ration the fluid solidifier 150 to only be used when wound fluid has activated it, based on the volume of exudates collected therein. Once the exudates contact the wall, the adhesive 152 releases the fluid solidifier 80 which in turn absorbs the wound fluid. The fluid solidifier 150 may be applied uniformly throughout the canister 60, in select portions therein, or in varying amounts, such as a concentration gradient of more to less from the top to the bottom of the canister 60.

As an alternative, the fluid solidifier 150 may be placed in the bottom of canister 60 as illustrated in FIG. 9 and covered and maintained with a water soluble film 154. The water soluble film 154 may be pre-formed or cured from a water soluble adhesive 152. For example, the water soluble adhesive 152 may be spread onto a slab and dried, by air or the addition of heat, to form film 154. The film may be of uniform or varying thickness. In embodiments, an adhesive may be used to fix the ends of the film 154 to canister 60. As illustrated in the present embodiment, the fluid solidifier 150 may be disposed in the canister 60 at an incline or slope relative to the bottom of canister 60. Accordingly, the film 154 may be thicker at a first end 155 relative to a second end 156 so that the exudates may flow down the include to the lowest available level of the collection canister 60 where any fluid solidifier 150 disposed therein may absorb the wound fluid.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art, and all such modifications and equivalents are believed to be within the spirit and scope of the disclosure as defined by the following claims.

What is claimed is:

1. A system to promote the healing of an exuding wound, which comprises:
    a vacuum source associated with a vacuum port; and
    a rigid collection canister having an interior wall defining an internal chamber in fluid communication with the vacuum source through the vacuum port, the collection canister defining a longitudinal axis and an orthogonal axis extending orthogonal to the longitudinal axis, the collection canister including a baffle mechanism disposed within the internal chamber for dampening movement of exudates collected from an exuding wound, the baffle mechanism including a first group of baffles, the baffles of the first group being arranged in spaced relation with respect to the longitudinal axis, and a second group of baffles, the baffles of the second group being arranged in spaced relation and in general orthogonal relation with respect to the longitudinal axis.

2. The system according to claim 1, wherein the baffle mechanism includes at least one antimicrobial treated material segment for controlling the growth of microorganisms in the exudates.

3. The system according to claim 2, wherein the material segment is anchored to the interior wall of the collection canister.

4. The system according to claim 1, wherein the baffles are dimensioned and arranged to impede flow of exudates within the chamber during ambulatory movement of the subject.

5. The system according to claim 1 wherein the baffles of the first group are arranged in general parallel relation with respect to the longitudinal axis.

6. The system according to claim 1 including a third group of baffles, the baffles of the third group being arranged in spaced relation with respect to the longitudinal axis.

7. The system according to claim 6 wherein the baffles of the third group are arranged in general diametrical opposed relation with respect to the baffles of the second group.

8. The system according to claim 1, further comprising a wound dressing dimensioned for positioning relative to a wound bed of a subject, the internal chamber of the canister being in fluid communication with the wound dressing for collecting exudates removed from the wound bed under influence of the vacuum source.

9. The system according to claim 2, wherein the material segment is configured to allow flow of liquids and gases therethrough.

10. The system according to claim 1, wherein the baffle mechanism is disposed within a lower section of the canister.

* * * * *